(12) United States Patent
Chang et al.

(10) Patent No.: US 10,422,784 B2
(45) Date of Patent: Sep. 24, 2019

(54) TESTING MODULE AND MEASURING APPARATUS HAVING THE SAME

(71) Applicant: CORETECH SYSTEM CO., LTD., Chupei, Hsinchu County (TW)

(72) Inventors: Yuing Chang, Chupei (TW); Rong-Yeu Chang, Chupei (TW); Chen-Chieh Wang, Chupei (TW); Chia-Hsiang Hsu, Chupei (TW)

(73) Assignee: CORETECH SYSTEM CO., LTD., Chupei, Hsinchu County (TW)

( * ) Notice: Subject to any disclaimer, the term of this patent is extended or adjusted under 35 U.S.C. 154(b) by 0 days.

(21) Appl. No.: 16/111,629

(22) Filed: Aug. 24, 2018

(65) Prior Publication Data

US 2019/0120815 A1 Apr. 25, 2019

Related U.S. Application Data

(60) Provisional application No. 62/574,988, filed on Oct. 20, 2017.

(51) Int. Cl.
*G01N 33/44* (2006.01)
*G01N 25/00* (2006.01)

(52) U.S. Cl.
CPC .......... *G01N 33/442* (2013.01); *G01N 25/00* (2013.01)

(58) Field of Classification Search
CPC ...... F01D 21/003; F01D 17/085; F01D 25/30; F01D 17/08; F01D 21/12; F01D 21/14; F01D 25/28; G01K 1/02; G01K 13/02; G01K 15/00; G01K 11/00; G01K 15/005; G01F 22/00; G01F 22/02; G01F 25/0084; G01F 25/0092; G01F 3/08; G01N 35/1016; G01N 1/2042; G01N 2291/02836;
(Continued)

(56) References Cited

U.S. PATENT DOCUMENTS 2,554,212 A * 5/1951 Quinlan .................. G01N 3/36
73/577
3,145,561 A * 8/1964 Thompson ............... G01N 7/00
196/132
(Continued)

FOREIGN PATENT DOCUMENTS

CN 204212986 U * 1/2015
CN 07713636 U * 10/2018

*Primary Examiner* — Gail Kaplan Verbitsky
(74) *Attorney, Agent, or Firm* — Muncy, Geissler, Olds & Lowe, P.C.

(57) ABSTRACT

A measuring apparatus includes a base and a testing module. The testing module is received in the base and includes a temperature-controlling bucket, a testing cylinder, and upper and lower pistons. The temperature-controlling bucket extends in a vertical direction and has a bucket wall having a bucket inner surface and a bucket outer surface opposite to the bucket inner surface. The testing cylinder extends in the vertical direction, is received in the temperature-controlling bucket, and has a cylinder wall having a cylinder inner surface and a cylinder outer surface opposite to the cylinder inner surface. The upper and lower pistons plug top and bottom ends of the testing cylinder, respectively. The upper piston has a receiving room located inside the upper piston, and has a piston temperature sensor and a piston heating wire received in the receiving room.

23 Claims, 12 Drawing Sheets

(58) Field of Classification Search
CPC ..... G01N 2035/1025; B01L 2200/0605; F04B 19/022
USPC .................... 374/141, 143, 4, 5, 45, 54, 100
See application file for complete search history.

(56) References Cited

U.S. PATENT DOCUMENTS

| | | | | |
|---|---|---|---|---|
| 3,206,977 | A * | 9/1965 | Mayer | G01F 1/74 |
| | | | | 177/155 |
| 3,670,576 | A * | 6/1972 | Corry | G01G 5/04 |
| | | | | 177/209 |
| 4,335,620 | A * | 6/1982 | Adams | G01N 1/18 |
| | | | | 422/64 |
| 4,425,810 | A * | 1/1984 | Simon | G01N 21/03 |
| | | | | 374/45 |
| 5,172,977 | A * | 12/1992 | Enustun | G01B 7/16 |
| | | | | 374/55 |
| 5,783,760 | A * | 7/1998 | Haines | G01N 15/082 |
| | | | | 73/865.6 |
| 5,992,222 | A * | 11/1999 | Belonenko | F04B 19/022 |
| | | | | 374/46 |
| 6,675,643 | B2 * | 1/2004 | Weissmann | G01F 17/00 |
| | | | | 73/149 |
| 7,716,964 | B2 * | 5/2010 | Kurtz | B64C 25/60 |
| | | | | 73/11.04 |
| 2011/0185809 | A1 * | 8/2011 | Guieze | G01N 1/2202 |
| | | | | 73/32 R |

* cited by examiner

US 10,422,784 B2

TESTING MODULE AND MEASURING APPARATUS HAVING THE SAME

PRIORITY CLAIM AND CROSS-REFERENCE

This application claims priority of U.S. provisional application Ser. No. 62/574,988 filed on Oct. 20, 2017, which is incorporated by reference in its entirety.

TECHNICAL FIELD

The present disclosure relates to measuring equipment, and more particularly, to a measuring apparatus designed for measuring volumetric variation under different temperatures and pressures.

DISCUSSION OF THE BACKGROUND

In the injection molding field, the volumetric variation of the plastic material directly affects the curvature and the shrinkage of the product. Normally, the volumetric variation of the plastic material is influenced by temperature and pressure during an injection molding operation. Therefore, it is important to understand relationships among the specific volume, temperature and pressure of the plastic material during the injection molding operation.

A conventional measuring apparatus for measuring the volumetric variation of the plastic material includes a base and a testing module. The testing module is received in the base and includes a bucket, a testing cylinder received in the bucket and receiving a testing sample, a heating unit connected to the bucket, and a piston plugging the testing cylinder. During a measuring operation, the density of the testing sample may lack uniformity due to non-uniform temperature distribution, and measurement errors may occur as a result. In addition, the non-uniform temperature distribution may also lead to interference between the piston and the testing cylinder. As a result, the piston may become jammed in the testing cylinder, or the testing sample may leak through a gap between the piston and the testing cylinder.

This Discussion of the Background section is for background information only. The statements in this Discussion of the Background are not an admission that the subject matter disclosed in this section constitutes a prior art to the present disclosure, and no part of this section may be used as an admission that any part of this application, including this Discussion of the Background section, constitutes prior art to the present disclosure.

SUMMARY

One aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The upper piston has a receiving room located inside the upper piston, and a piston temperature sensor and a piston heating wire are received in the receiving room.

In some embodiments, a diameter of the cylinder outer surface of the testing cylinder is greater than a diameter of the bucket inner surface of the temperature-controlling bucket.

In some embodiments, the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire. In some embodiments, the bucket heating wire and the cooling pipe are spirally extended. In some embodiments, the wire groove has a semicircular cross-section.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

In some embodiments, the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire. In some embodiments, the bucket heating wire and the cooling pipe are spirally extended. In some embodiments, the wire groove has a semicircular cross-section.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

Another aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. A diameter of the cylinder outer surface of the testing cylinder is greater than a diameter of the bucket inner surface of the temperature-controlling bucket.

In some embodiments, the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire. In some embodiments, the bucket heating wire and the cooling pipe are spirally extended. In some embodiments, the wire groove has a semicircular cross-section.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

Still another aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire. The bucket heating wire and the cooling pipe are spirally extended. The wire groove has a semicircular cross-section.

In some embodiments, the testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

Another aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The testing cylinder further has a chamber defined by the cylinder wall, a plurality of sensor grooves formed in the cylinder outer surface of the cylinder wall, and a plurality of cylinder temperature sensors respectively received in the sensor grooves.

In some embodiments, a diameter difference between the chamber of the testing cylinder and the upper piston is between 1 and 5 micrometers.

With the above configurations of the measuring apparatus, measurement errors can be eliminated, and leakage of the testing sample can be prevented. In addition, the upper piston can be prevented from being jammed in the testing cylinder. Consequently, the drawbacks of the conventional measuring apparatus can be alleviated.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

References to "some embodiments of the present disclosure," "an embodiment," "exemplary embodiment," "other embodiments of the present disclosure," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may.

The present disclosure is directed to a measuring apparatus for measuring volumetric variation under different temperatures and pressures. In order to make the present disclosure completely comprehensible, detailed steps and structures are provided in the following description. Obviously, implementation of the present disclosure does not limit special details known by persons skilled in the art. In addition, known structures and steps are not described in detail, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed description, and is defined by the claims.

Figure 1:
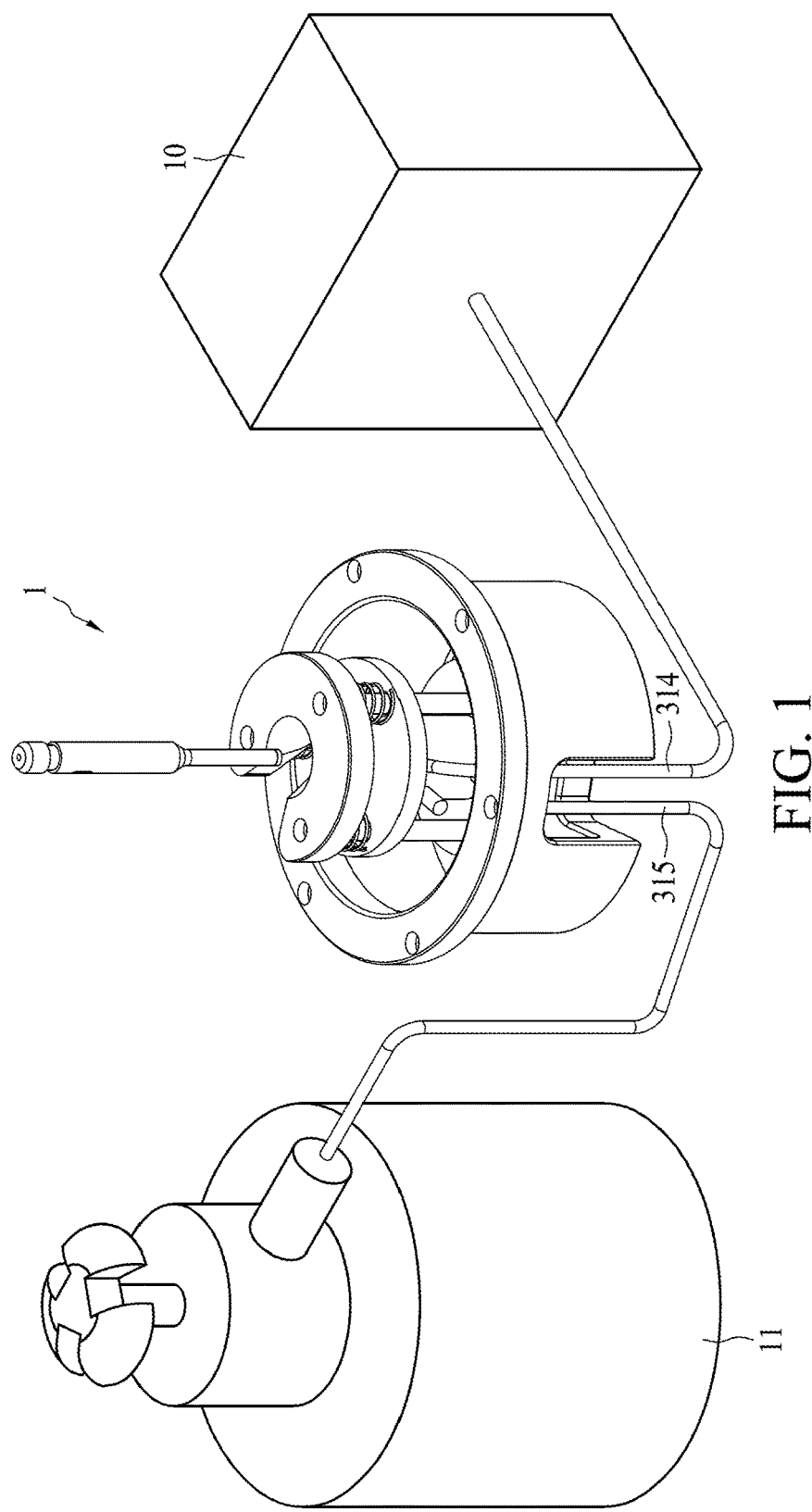
FIG. 1 is a schematic view illustrating a measuring apparatus connected to a cooling fluid tank and a fluid exhaust container in accordance with some embodiments of the present disclosure.
Figure 2:
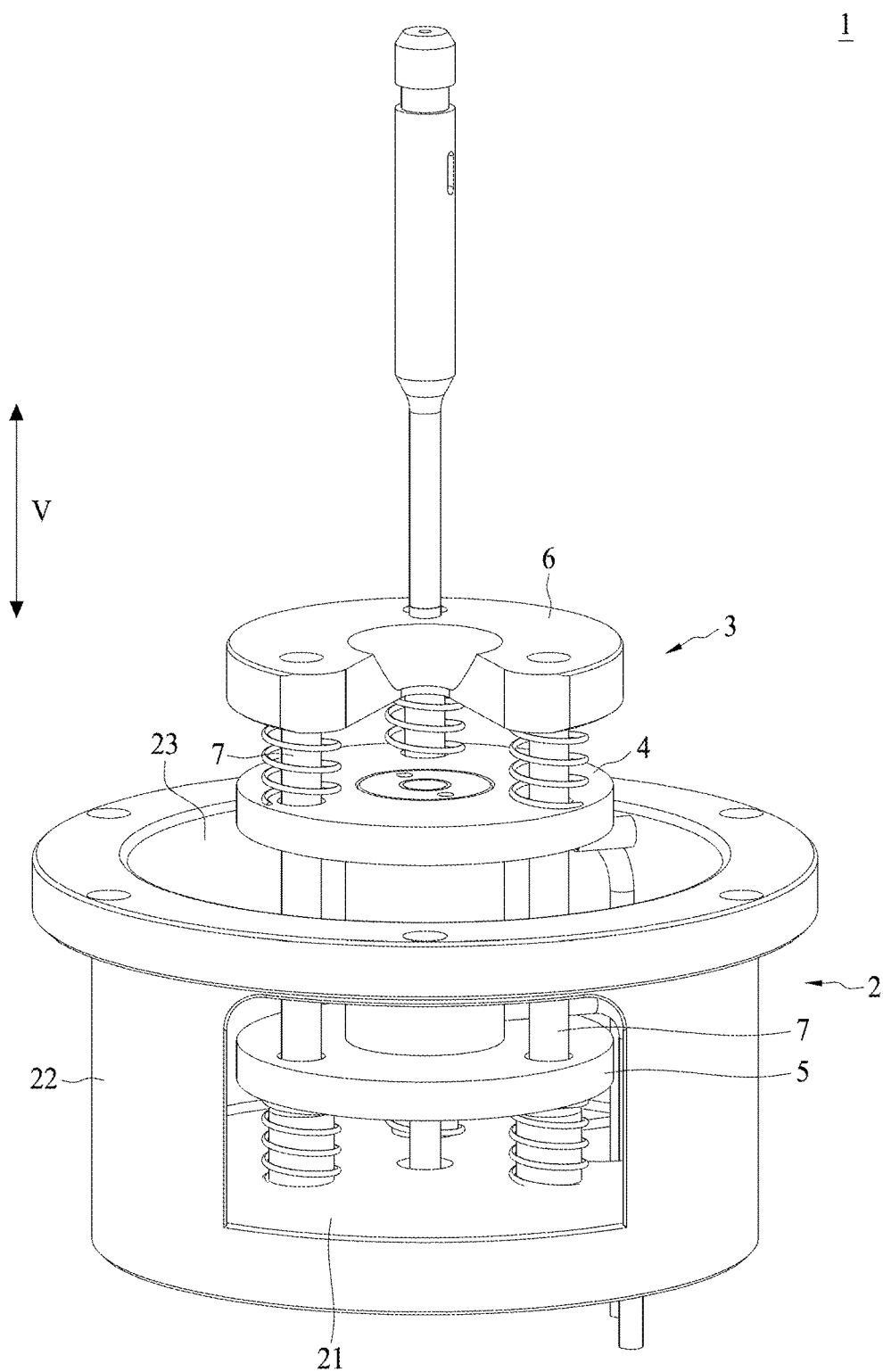
FIG. 2 is a top perspective view of the measuring apparatus in accordance with some embodiments of the present disclosure.
Figure 3:
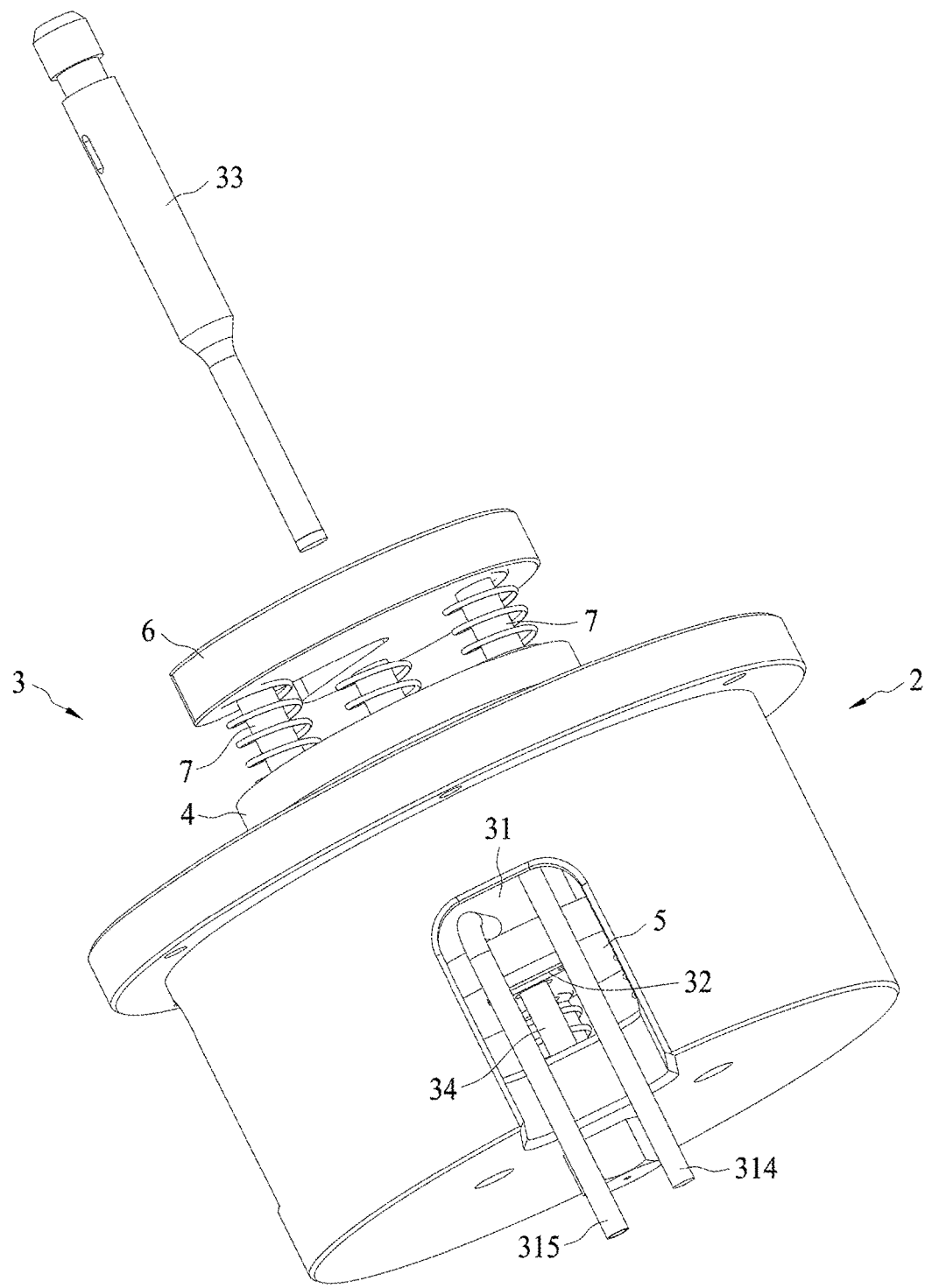
FIG. 3 is a bottom perspective view of the measuring apparatus in accordance with some embodiments of the present disclosure.

FIG. 1 is a schematic view illustrating a measuring apparatus 1 connected to a cooling fluid tank 10 and a fluid exhaust container 11 in accordance with some embodiments of the present disclosure; FIG. 2 is a top perspective view of the measuring apparatus 1 in accordance with some embodiments of the present disclosure; FIG. 3 is a bottom perspective view of the measuring apparatus 1 in accordance with some embodiments of the present disclosure; and FIG. 4 is an exploded perspective view of the measuring apparatus 1 in accordance with some embodiments of the present disclosure.

In some embodiments, referring to FIG. 1, FIG. 2, FIG. 3 and FIG. 4, the measuring apparatus 1 includes a base 2, a testing module 3, a top cover 4, a bottom cover 5, a guiding member 6 and a plurality of supporting rods 7. The base 2 has a base bottom wall 21, and a base surrounding wall 22 extending from a periphery of the base bottom wall 21, and combining with the base bottom wall 21 to form a receiving space 23 disposed for receiving the testing module 3.

Figure 4:
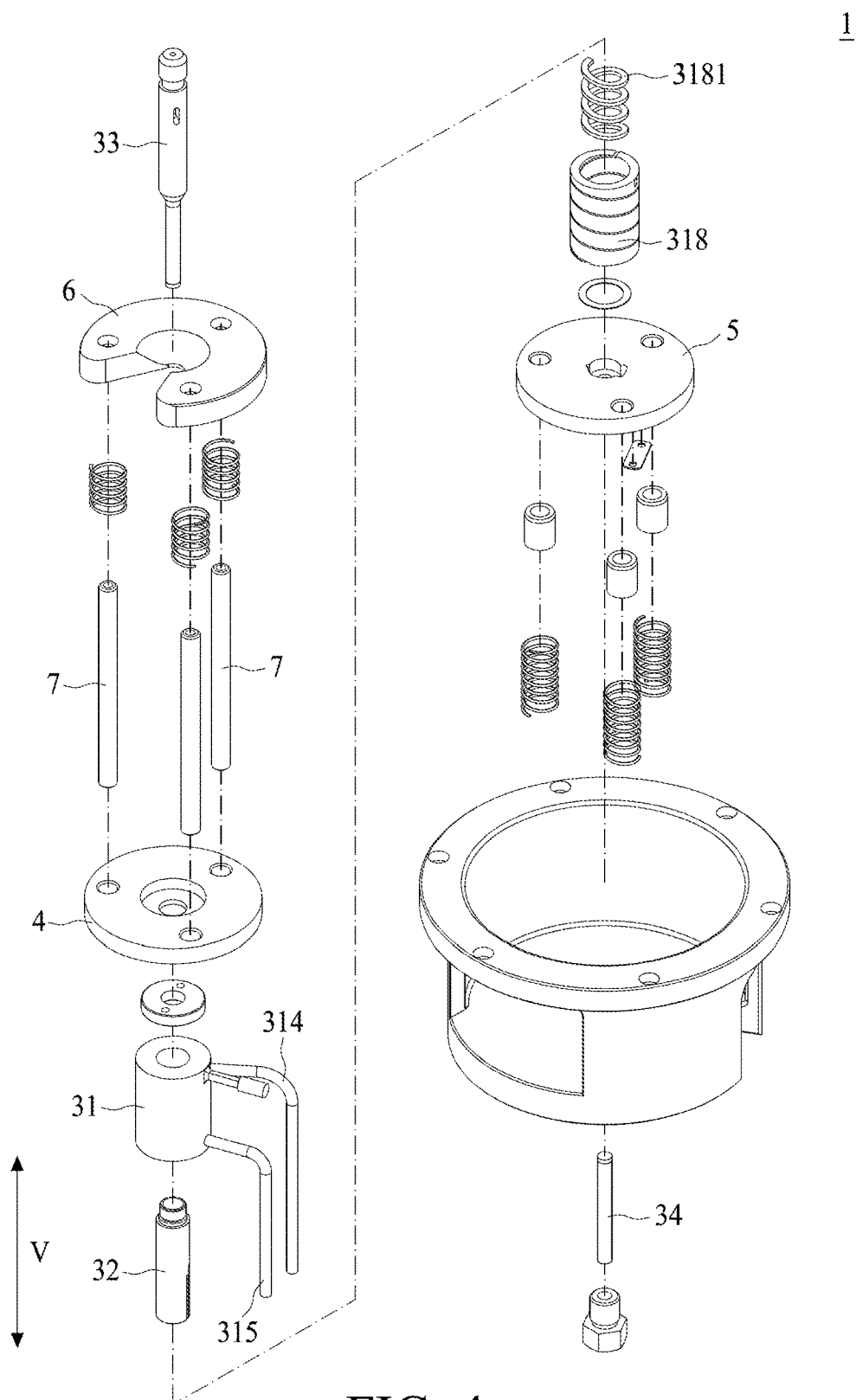
FIG. 4 is an exploded perspective view of the measuring apparatus in accordance with some embodiments of the present disclosure.

Referring to FIG. 4, in some embodiments, the testing module 3 includes a temperature-controlling bucket 31 extending in a vertical direction (V); a testing cylinder 32 extending in the vertical direction and received in the temperature-controlling bucket 31; and upper and lower pistons 33, 34 respectively plugging top and bottom ends of the testing cylinder 32.

Referring to FIG. 4, in some embodiments, the top and bottom covers 4, 5 are respectively mounted to the top and bottom ends of the testing cylinder 32 for holding the testing cylinder 32. In some embodiments, the guiding member 6 is disposed on the top cover 4 for guiding the insertion of the upper piston 33. In some embodiments, the guiding rods 7 extend in the vertical direction from the base bottom wall 21 of the base 2 through the top and bottom covers 4, 5 to the guiding member 6 and are disposed for firmly fixing the guiding member 6 and the top and bottom covers 4, 5.

Figure 5:
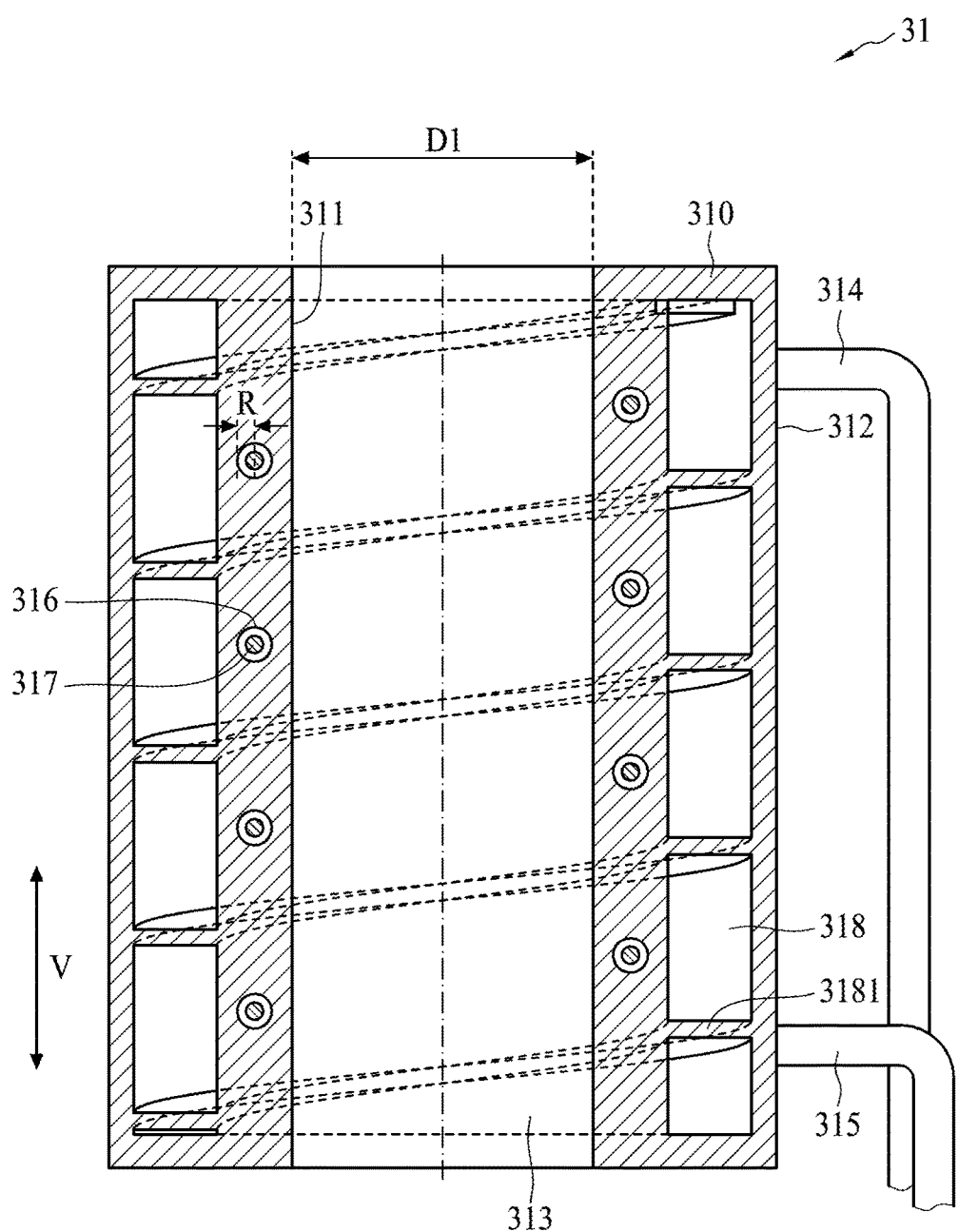
FIG. 5 is a side sectional schematic view of a temperature-controlling bucket of the measuring apparatus in accordance with some embodiments of the present disclosure.

FIG. 5 is a sectional view of the temperature-controlling bucket 31 of the measuring apparatus 1 in accordance with some embodiments of the present disclosure. In some embodiments, referring to FIG. 1, FIG. 4 and FIG. 5, the temperature-controlling bucket 31 has a bucket wall 310 having a bucket inner surface 311 and a bucket outer surface 312 that is opposite to the bucket inner surface 311; a receiving hole 313 defined by the bucket wall 310 and disposed for receiving the testing cylinder 32; a cooling fluid inlet 314 and a cooling fluid outlet 315 respectively connected to the cooling fluid tank 10 and the fluid exhaust container 11; a wire groove 316 formed in one of the bucket inner surface 311 of the temperature-controlling bucket 31 and the testing cylinder 32; a bucket heating wire 317 received in the wire groove 316; and a cooling pipe 318 disposed in the bucket wall 310 and having two opposite ends that are respectively connected to the cooling fluid inlet 314 and the cooling fluid outlet 315, and surrounding the bucket heating wire 317. In some embodiments, the cooling pipe 318 further has a pipe spacer 3181 disposed for spacing coils of the cooling pipe 318. In some embodiments, the cooling pipe 318 is disposed for allowing a cooling fluid to flow therethrough. In some embodiments, the heating rate and the cooling rate of a testing sample can both be adjusted by changing the flow rate of the cooling fluid in the cooling pipe 318.

Figure 6:
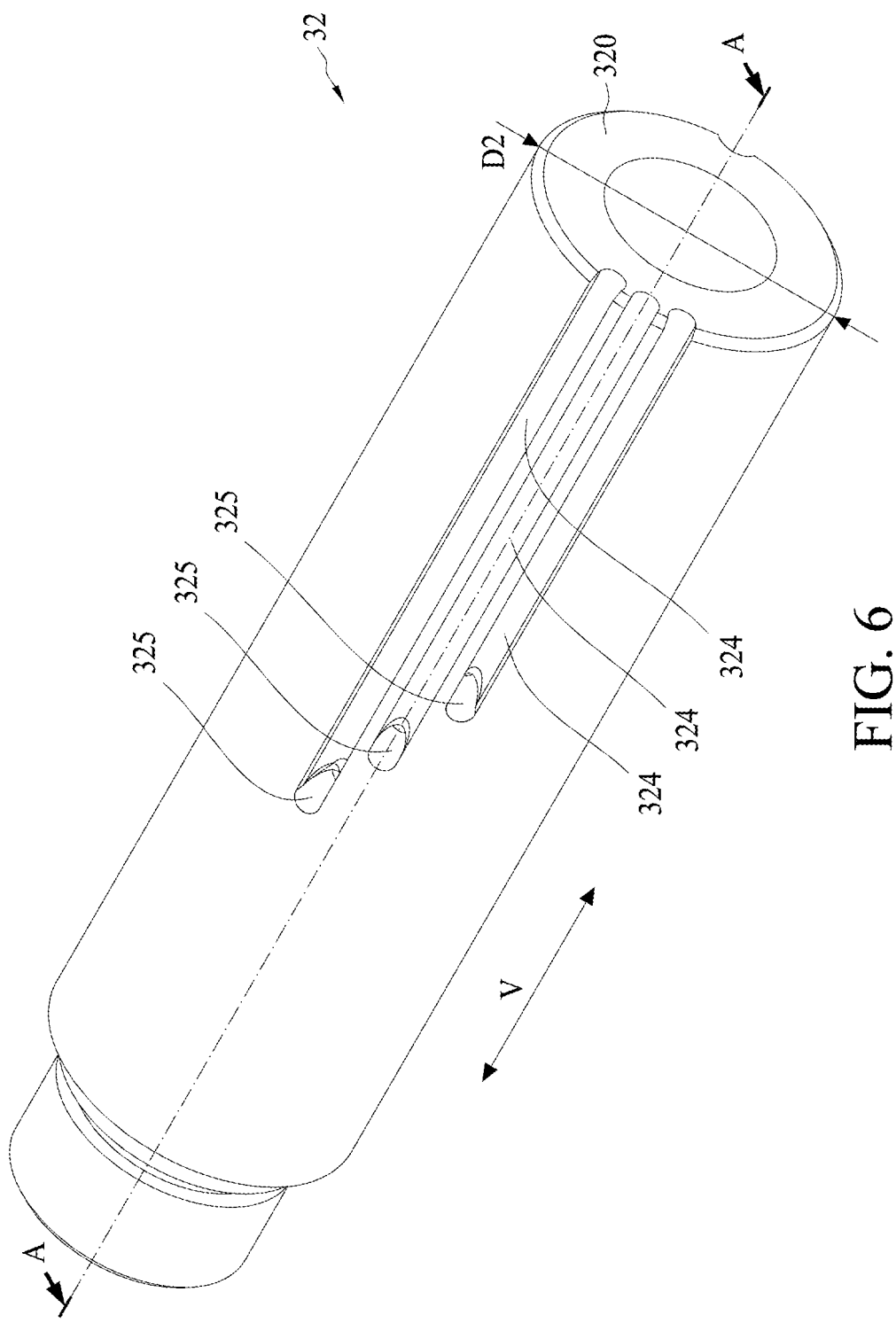
FIG. 6 is a perspective view of a testing cylinder of the measuring apparatus in accordance with some embodiments of the present disclosure.
Figure 7:
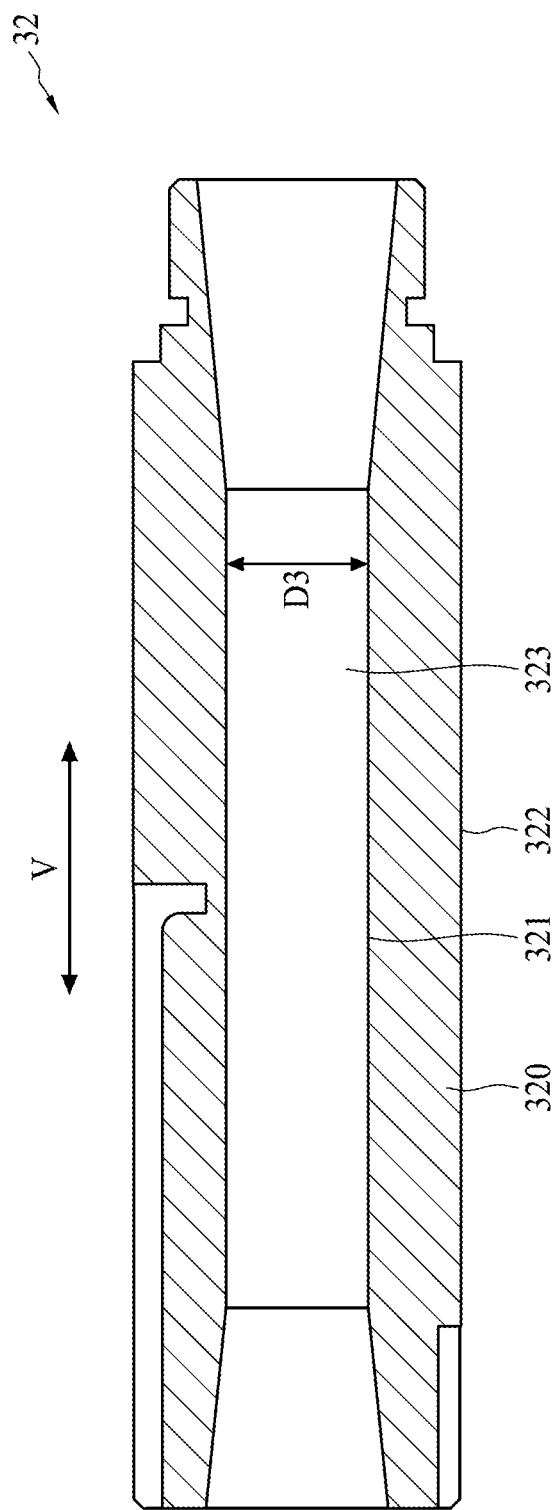
FIG. 7 is a sectional view taken along line A-A in FIG. 6.

FIG. 6 is a perspective view of the testing cylinder 32 of the measuring apparatus 1 in accordance with some embodiments of the present disclosure, and FIG. 7 is a sectional view taken along line A-A in FIG. 6. In some embodiments, referring to FIG. 5, FIG. 6 and FIG. 7, the testing cylinder 32 has a cylinder wall 320 having a cylinder inner surface 321 and a cylinder outer surface 322 that is opposite to the cylinder inner surface 321; a chamber 323 defined by the cylinder wall 320 and disposed for receiving the testing sample; a plurality of sensor grooves 324 formed in the cylinder wall 320; and a plurality of cylinder temperature sensors 325 respectively received in the sensor grooves 324. In some embodiments, the wire groove 316 is formed in one of the bucket inner surface 311 of the temperature-controlling bucket 31 and the cylinder outer surface 322 of the testing cylinder 32. In some embodiments, a diameter (D2) of the cylinder outer surface 322 of the testing cylinder 32 is slightly greater than a diameter (D1) of the bucket inner surface 311 of the temperature-controlling bucket 31, such that there will be no gap between the temperature-controlling bucket 31 and the testing cylinder 32 even if the testing cylinder 32 is under high temperature.

Figure 8A:
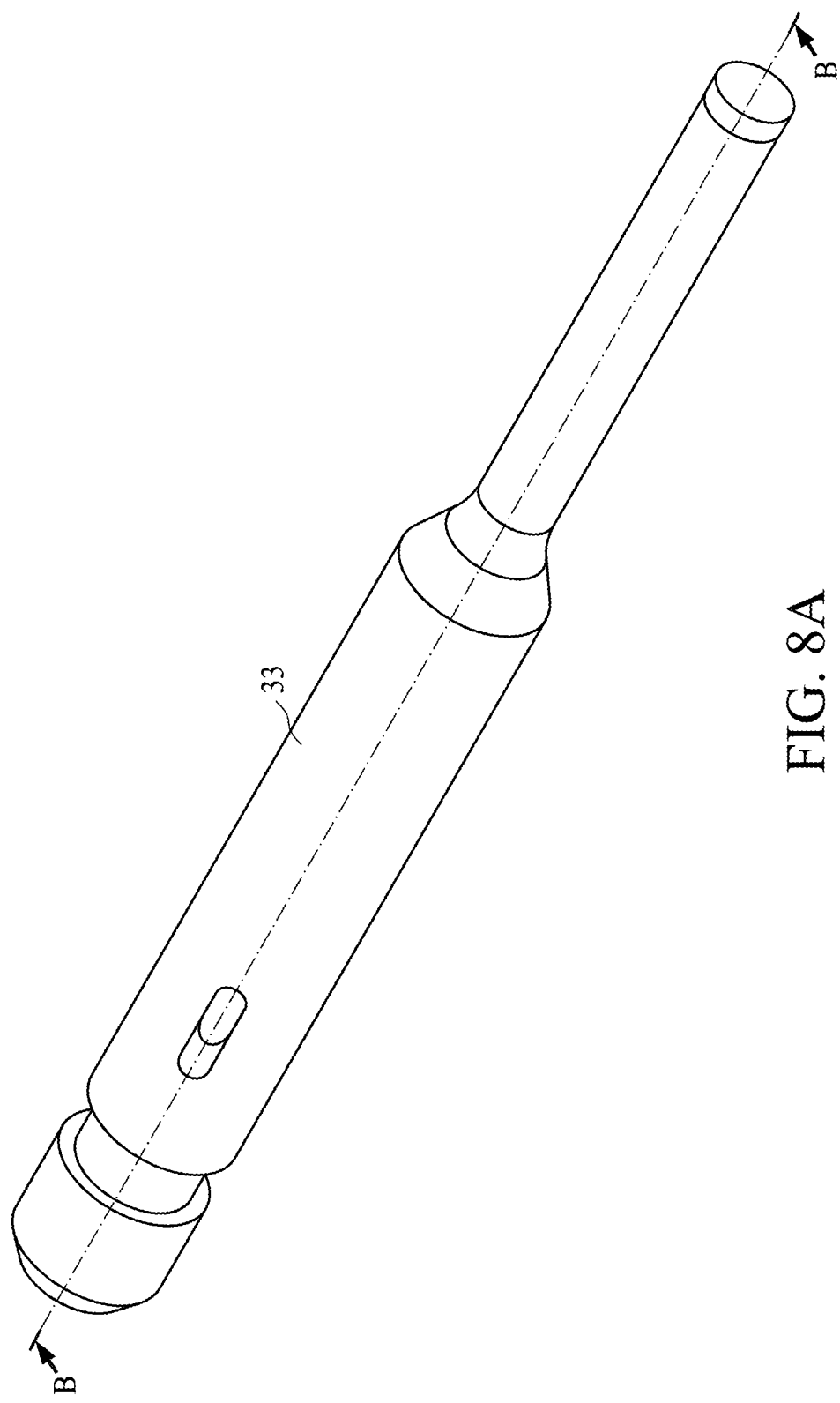
FIG. 8A is a perspective view of an upper piston of the measuring apparatus in accordance with some embodiments of the present disclosure.
Figure 8B:
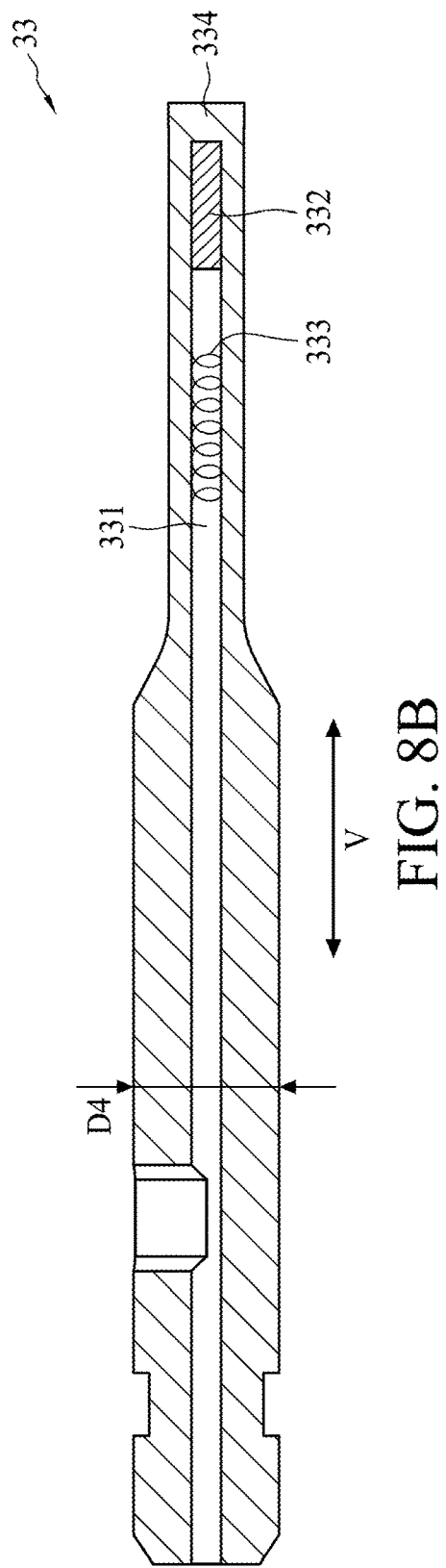
FIG. 8B is a sectional view taken along line B-B in FIG. 8A.

FIG. 8A is a perspective view of the upper piston 33 of the measuring apparatus 1 in accordance with some embodiments of the present disclosure, and FIG. 8B is a sectional view taken along line B-B in FIG. 8A. In some embodiments, referring to FIG. 7, FIG. 8A and FIG. 8B, the upper piston 33 has a receiving room 331 located inside the upper piston 33; a piston temperature sensor 332 and a piston heating wire 333 both received in the receiving room 331 and both disposed for actively controlling the temperature of the upper piston 33 to be held at the same temperature as the testing cylinder 32 and the testing sample so as to implement the uniform temperature distribution. In some embodiments, a piston end 334 is coated with dual layers, and the disposition of the dual layers is intended to increase the hardness of the piston end 334 so as to improve the wear resistance of the piston end 334 and to prolong the service life of the upper piston 33.

In some embodiments, a diameter (D3) of the chamber 323 of the testing cylinder 32 is slightly greater than a maximum diameter (D4) of the upper piston 33. In some embodiments, the maximum diameter of the upper piston 33 can be slightly adjusted by changing the temperature through the piston heating wire 333 so as to adjust the diameter difference between the chamber 323 of the testing cylinder 32 and the upper piston 33; consequently, gas is allowed to leak through a gap between the testing cylinder 32 and the upper piston 33, while the testing sample under test is prevented from leaking through the gap between the testing cylinder 32 and the upper piston 33. In some embodiments, slightly adjusting the size of the upper piston 33 by changing the temperature can also prevent the upper piston 33 from becoming jammed in the chamber 323 of the testing cylinder 32. In some embodiments, the dispositions of the upper and lower pistons 33, 34 can also serve to retain the testing sample in the chamber 323 of the testing cylinder 32.

In some embodiments, referring to FIG. 7 and FIG. 8A, the diameter difference between the chamber 323 of the testing cylinder 32 and the upper piston 33 is between 1 and 5 micrometers. In other embodiments, the diameter difference between the chamber 323 and the upper piston 33 may vary within other ranges.

Referring back to FIG. 4 and FIG. 5, in the exemplary embodiment, the wire groove 316 is formed in the bucket inner surface 311 of the temperature-controlling bucket 31 and has a semicircular cross-section and a radius (R) between 0.02 and 0.06 millimeters; the wire groove 316 and the cooling pipe 318 are spirally extended to implement uniform temperature distribution; space between coils of the bucket heating wire 317 is adjustable to implement the uniform temperature distribution; and the bucket heating wire 317 is encapsulated by cast iron. In other embodiments, such arrangements may be varied.

Referring back to FIG. 6 and FIG. 7, in the exemplary embodiment, the testing cylinder 32 has three sensor grooves 324 respectively formed in the cylinder outer surface 322 at upper, middle and lower portions, and three cylinder temperature sensors 325 respectively received in the sensor grooves 324. With such arrangement, the temperature of the testing sample can be precisely measured. In some embodiments, the design of forming the sensor grooves 324 in the cylinder outer surface 322 of the testing cylinder 32, rather than embedding the sensor grooves 324 inside the cylinder wall 320 of the testing cylinder 32, can prevent the testing cylinder 32 from distortion under high temperature and high pressure, i.e., substantially maintaining the cross-section of the testing cylinder 32. In other embodiments, the quantities of the sensor grooves 324 and the cylinder temperature sensors 325, and the arrangement of the sensor grooves 324, may be varied.

Referring back to FIG. 8, in the exemplary embodiment, the dual layers of the upper piston 33 are made of chromium nitride, but in other embodiments the dual layers of the upper piston 33 may be made of other materials.

During a measuring operation, referring back to FIG. 4, FIG. 5, FIG. 6 and FIG. 7, in the exemplary embodiment, the bottom piston 34 first plugs the bottom end of the testing cylinder 32, the testing sample is then disposed in the chamber 323, and the upper piston 33 is then slid through the guiding member 6 to plug the top end of the testing cylinder 32. The bucket heating wire 317 subsequently heats the testing cylinder 32 to a desired heating temperature. When the bucket heating wire 317 heats the testing cylinder 32, the cylinder temperature sensors 325 can monitor the temperature of the testing cylinder 32 in real time. The cooling fluid flows through the cooling pipe 318 to control the heating rate of the testing sample, and, simultaneously, the piston heating wire 333 of the upper piston 33 heats the upper piston 33 to maintain the temperature balance between the testing cylinder 32 and the upper piston 33. After the desired heating temperature of the testing cylinder 32 is reached, the bucket heating wire 317 stops heating the testing cylinder 32, and the flowing of the cooling fluid then helps the testing cylinder 32 to rapidly cool down to a desired cooling temperature. In some embodiments, as the temperature of the testing cylinder 32 varies, the pressure in the testing cylinder 32 also changes. For example, when the temperature of the testing cylinder 32 reaches the desired heating temperature, the pressure in the testing cylinder 32 is also high, and when the temperature of the testing cylinder 32 drops to the desired cooling temperature, the pressure in the testing cylinder 32 is low. Thus, the volumetric variation of the testing sample can be measured under different temperatures and pressures through the measuring operation.

Figure 9:
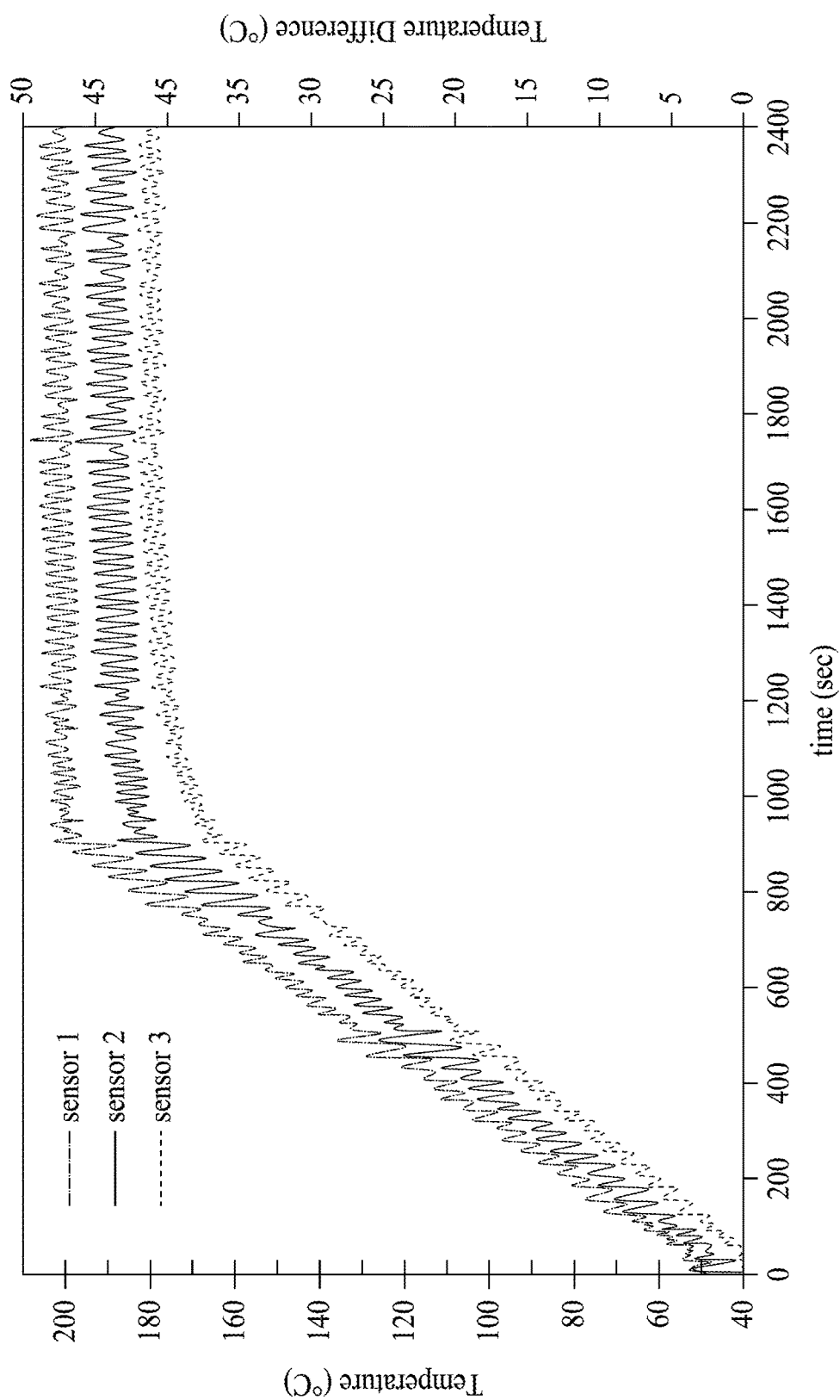
FIG. 9 is a schematic plot showing an updated temperature profile of a testing cylinder of a comparative measuring apparatus.

FIG. 9 is a schematic plot showing an updated temperature profile of a testing cylinder of a comparative measuring apparatus. Each of the data lines in FIG. 9 represents a respective one of cylinder temperature sensors of the comparative measuring apparatus and shows a plurality of temperature values corresponding to different times. At a given fixed time, temperature differences among the cylinder temperature sensors can be observed, indicating non-uniform temperature distribution.

Figure 10:
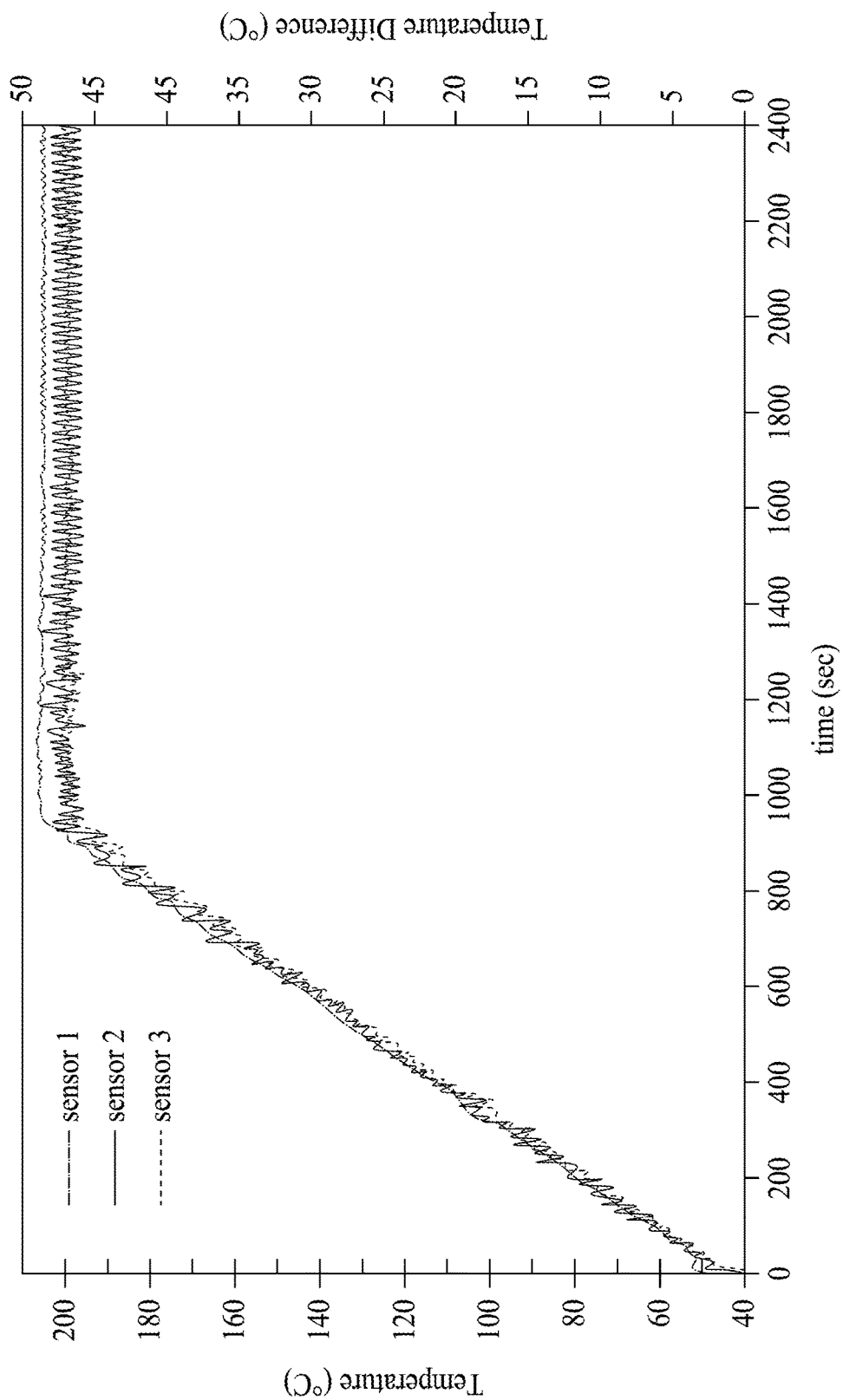
FIG. 10 is a schematic plot showing an updated temperature profile of the testing cylinder of the measuring apparatus in accordance with some embodiments of the present disclosure.

FIG. 10 is a schematic plot showing an updated temperature profile of the testing cylinder 32 of the measuring apparatus 1 in accordance with some embodiments of the present disclosure. Compared with FIG. 9, in the exemplary embodiment, at a given fixed time, temperature differences among the three cylinder temperature sensors 325 are greatly reduced, affirming that with the disposition of the spirally-extended bucket heating wire 317, the uniform temperature distribution can be fully achieved.

Figure 11:
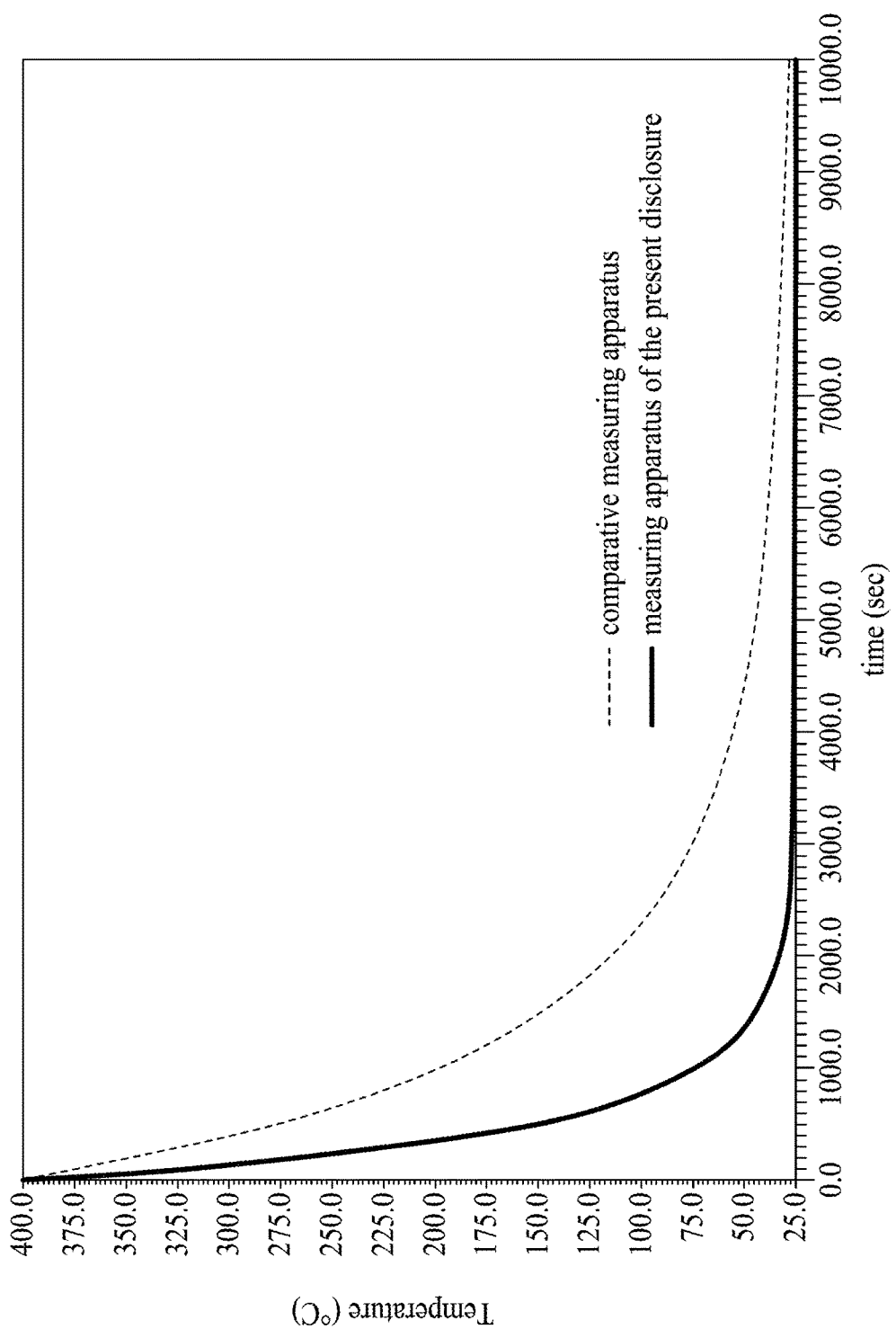
FIG. 11 is a schematic plot showing an updated temperature profile that illustrates different cooling rates of a testing sample under different conditions.

FIG. 11 is a schematic plot showing an updated temperature profile that compares different cooling rates of the testing sample. The dashed data line represents a plurality of temperature values corresponding to different times at which the testing sample is received in the comparative measuring apparatus, and the solid data line represents a plurality of temperature values corresponding to different times at which the testing sample is received in the measuring apparatus 1 of the present disclosure. As can be observed from the updated temperature profile in FIG. 11, in the exemplary embodiment, the time required for the measuring apparatus 1 to cool down to the desired cooling temperature is less than the time required for the comparative measuring apparatus to cool down to the desired cooling temperature. This affirms that the disposition of the spirally-extended cooling pipe 318, as shown in FIG. 5, can greatly reduce the cooling time. In some embodiments, with the reduced cooling time, both the effectiveness and the efficiency of the measuring operation can be improved.

In conclusion, with the size arrangements of the temperature-controlling bucket 31 and the testing cylinder 32, it can be assured that there is no gap between the temperature-controlling bucket 31 and the testing cylinder 32 under high temperature. In addition, the configuration of the upper piston 33 allows gas to leak through the gap between the testing cylinder 32 and the upper piston 33, while preventing the testing sample under test from leaking through the gap between the testing cylinder 32 and the upper piston 33. Moreover, a spacer is not required to be disposed in the measuring apparatus 1, thereby eliminating the error that otherwise can originate from the compression and expansion of the spacer under different temperatures and pressures.

One aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The upper piston has a receiving room located inside the upper piston, and a piston temperature sensor and a piston heating wire are received in the receiving room.

One aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. A diameter of the cylinder outer surface of the testing cylinder is greater than a diameter of the bucket inner surface of the temperature-controlling bucket.

One aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire. The bucket heating wire and the cooling pipe are spirally extended. The wire groove has a semicircular cross-section.

One aspect of the present disclosure provides a measuring apparatus that is designed for measuring volumetric variation under different temperatures and pressures, that can prevent measurement errors, and that can prevent the leakage of a testing sample under test. The measuring apparatus comprises a testing module comprising a temperature-controlling bucket, a testing cylinder and upper and lower pistons. The temperature-controlling bucket extends in a vertical direction and comprises a bucket wall having a bucket inner surface and a bucket outer surface opposite to the bucket inner surface. The testing cylinder extends in the vertical direction, is received in the temperature-controlling bucket, and comprises a cylinder wall having a cylinder inner surface and a cylinder outer surface opposite to the cylinder inner surface. The upper and lower pistons respectively plug top and bottom ends of the testing cylinder. The testing cylinder further has a chamber defined by the cylinder wall, a plurality of sensor grooves formed in the cylinder outer surface of the cylinder wall, and a plurality of cylinder temperature sensors respectively received in the sensor grooves.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A measuring apparatus for measuring volumetric variation of a liquid under different temperatures and pressures, comprising:
   a testing module, comprising:
      a temperature-controlling bucket extending in a vertical direction and heating and cooling a testing cylinder, wherein the temperature-controlling bucket comprises a bucket wall having a bucket inner surface and a bucket outer surface opposite to the bucket inner surface;
      the testing cylinder extending in the vertical direction and receiving the liquid therein, wherein the testing cylinder is received in the temperature-controlling bucket and comprises a cylinder wall having a cylinder inner surface and a cylinder outer surface opposite to the cylinder inner surface, the liquid in the testing cylinder is heated and cooled by the temperature-controlling bucket; and
      upper and lower pistons that respectively plug top and bottom ends of the testing cylinder;
   wherein the upper piston has a receiving room located inside the upper piston, and a piston temperature sensor and a piston heating wire are received in the receiving room, and
   wherein the volumetric variation of the liquid is measured based on a state of the liquid under different temperatures and pressures of the liquid.

2. The measuring apparatus as claimed in claim 1, wherein a diameter of the cylinder outer surface of the testing cylinder is greater than a diameter of the bucket inner surface of the temperature-controlling bucket.

3. The measuring apparatus as claimed in claim 2, wherein:
   the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire;
   the bucket heating wire and the cooling pipe are spirally extended; and
   the wire groove has a semicircular cross-section.

4. The measuring apparatus as claimed in claim 3, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

5. The measuring apparatus as claimed in claim 4, wherein a diameter difference between the chamber of the testing cylinder and the upper piston is between 1 and 5 micrometers.

6. The measuring apparatus as claimed in claim 2, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

7. The measuring apparatus as claimed in claim 6, wherein a diameter difference between the chamber of the testing cylinder and the upper piston is between 1 and 5 micrometers.

8. The measuring apparatus as claimed in claim 1, wherein:
   the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire;
   the bucket heating wire and the cooling pipe are spirally extended; and
   the wire groove has a semicircular cross-section.

9. The measuring apparatus as claimed in claim 8, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

10. The measuring apparatus as claimed in claim 9, wherein a diameter difference between the chamber of the testing cylinder and the upper piston is between 1 and 5 micrometers.

11. The measuring apparatus as claimed in claim 1, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

12. The measuring apparatus as claimed in claim 11, wherein a diameter difference between the chamber of the testing cylinder and the upper piston is between 1 and 5 micrometers.

13. A measuring apparatus for measuring volumetric variation of a material under different temperatures and pressures, comprising:
   a testing module, comprising:
      a temperature-controlling bucket extending in a vertical direction, wherein the temperature-controlling bucket comprises a bucket wall having a bucket inner surface and a bucket outer surface opposite to the bucket inner surface;
      a testing cylinder extending in the vertical direction, wherein the testing cylinder is received in the temperature-controlling bucket and comprises a cylinder wall having a cylinder inner surface and a cylinder outer surface opposite to the cylinder inner surface; and
      upper and lower pistons that respectively plug top and bottom ends of the testing cylinder;
   wherein a diameter of the cylinder outer surface of the testing cylinder is greater than a diameter of the bucket inner surface of the temperature-controlling bucket and wherein the volumetric variation of the liquid is measured based on a state of the liquid under different temperatures and pressures of the liquid.

14. The measuring apparatus as claimed in claim 13, wherein:
   the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire;

the bucket heating wire and the cooling pipe are spirally extended; and the wire groove has a semicircular cross-section.

15. The measuring apparatus as claimed in claim 14, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

16. The measuring apparatus as claimed in claim 15, wherein a diameter difference between the chamber of the testing cylinder and the upper piston is between 1 and 5 micrometers.

17. The measuring apparatus as claimed in claim 13, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

18. The measuring apparatus as claimed in claim 17, wherein a diameter difference between the chamber of the testing cylinder and the upper piston is between 1 and 5 micrometers.

19. A measuring apparatus for measuring volumetric variation of a material under different temperatures and pressures, comprising:

a testing module, comprising:

a temperature-controlling bucket extending in a vertical direction, wherein the temperature-controlling bucket comprises a bucket wall having a bucket inner surface and a bucket outer surface opposite to the bucket inner surface;

a testing cylinder extending in the vertical direction, wherein the testing cylinder is received in the temperature-controlling bucket and comprises a cylinder wall having a cylinder inner surface and a cylinder outer surface opposite to the cylinder inner surface; and upper and lower pistons that respectively plug top and bottom ends of the testing cylinder;

wherein the temperature-controlling bucket further has a receiving hole defined by the bucket wall and disposed for receiving the testing cylinder, a wire groove formed in one of the bucket inner surface of the temperature-controlling bucket and the cylinder outer surface of the testing cylinder, a bucket heating wire received in the wire groove, and a cooling pipe disposed in the bucket wall and surrounding the bucket heating wire;

wherein the bucket heating wire and the cooling pipe are spirally extended;

wherein the wire groove has a semicircular cross-section, and wherein the volumetric variation of the liquid is measured based on a state of the liquid under different temperatures and pressures of the liquid.

20. The measuring apparatus as claimed in claim 19, wherein the testing cylinder further has a chamber defined by the cylinder wall, a plurality of sensor grooves formed in the cylinder outer surface of the cylinder wall, and a plurality of cylinder temperature sensors respectively received in the sensor grooves.

21. The measuring apparatus as claimed in claim 20, wherein a diameter difference between the chamber of the testing cylinder and the upper piston is between 1 and 5 micrometers.

22. A measuring apparatus for measuring volumetric variation of a liquid under different temperatures and pressures, comprising:

a testing module, comprising:

a temperature-controlling bucket extending in a vertical direction and heating and cooling a testing cylinder, wherein the temperature-controlling bucket comprises a bucket wall having a bucket inner surface and a bucket outer surface opposite to the bucket inner surface;

the testing cylinder extending in the vertical direction and receiving the liquid therein, wherein the testing cylinder is received in the temperature-controlling bucket and comprises a cylinder wall having a cylinder inner surface and a cylinder outer surface opposite to the cylinder inner surface, the liquid in the testing cylinder is heated and cooled by the temperature-controlling bucket; and upper and lower pistons that respectively plug top and bottom ends of the testing cylinder;

wherein the testing cylinder further has a chamber defined by the cylinder wall to receive the liquid, a plurality of sensor grooves formed in the cylinder outer surface of the cylinder wall, and a plurality of cylinder temperature sensors respectively received in the sensor grooves, and wherein the volumetric variation of the liquid is measured based on a state of the liquid under different temperatures and pressures of the liquid.

23. The measuring apparatus as claimed in claim 22, wherein a diameter difference between the chamber of the testing cylinder and the upper piston is between 1 and 5 micrometers.

\* \* \* \* \*